(12) United States Patent
Lewandowski (10) Patent No.: US 7,131,946 B2
(45) Date of Patent: Nov. 7, 2006

(54) ULTRASONIC DETECTION OF EAR DISORDERS

(75) Inventor: Jan Lewandowski, South Euclid, OH (US)

(73) Assignee: Biomec, Inc., Cleveland, OH (US)

( * ) Notice: Subject to any disclaimer, the term of this patent is extended or adjusted under 35 U.S.C. 154(b) by 0 days.

(21) Appl. No.: 10/729,741

(22) Filed: Dec. 5, 2003

(65) Prior Publication Data

US 2004/0133108 A1    Jul. 8, 2004

Related U.S. Application Data

(60) Provisional application No. 60/432,191, filed on Dec. 6, 2002, provisional application No. 60/442,869, filed on Jan. 27, 2003.

(51) Int. Cl.
    *A61B 8/00*    (2006.01)

(52) U.S. Cl. .................. 600/438; 600/459; 600/559

(58) Field of Classification Search ........ 600/437–438, 600/449, 454–459, 462–463, 559, 586, 200, 600/379, 473
See application file for complete search history.

(56) References Cited

U.S. PATENT DOCUMENTS

| | | | | |
|---|---|---|---|---|
| 5,546,956 | A | * | 8/1996 | Thornton .................. 600/559 |
| 5,669,388 | A | * | 9/1997 | Vilkomerson .............. 600/454 |
| 5,921,928 | A | | 7/1999 | Greenleaf et al. |
| 5,941,825 | A | * | 8/1999 | Lang et al. ................ 600/449 |
| 6,093,150 | A | * | 7/2000 | Chandler et al. .......... 600/459 |
| 6,102,860 | A | | 8/2000 | Mooney |

(Continued)

OTHER PUBLICATIONS

Christopher M. Discolo, Michael C. Byrd, Theresa Bates, Don Hazony, Jan Lewandowski and Peter J. Koltai, "Ultrasonic Detection of Middle Ear Effusion", American Medical Association, 2004, pp. 1407-1410.

"Real-time B-scan Ultrasound in Middle Ear Assessment" A Preliminary Report, by Lynn S. Alvord, PhD, Perry G. Fine, MD, pp. 91-94, © 1990 by the American Institute of Ultrasound in Medicine.

"Ultrasonics in Otolaryngology", An Aid in the Disgnosis of Middle Ear Fluid, by David H. Abramson, MD, Allan L. Abramson, MD and D. Jackson Coleman, MD, New York, pp. 146-160, Arch Otolaryng, vol. 96, Aug. 1972.

"Uses of Ultrasound in Audiology", by Lynn S. Alvord, Journal of American Academy of Audiology, vol. 1, No. 4, pp. 227-235, Oct. 1990.

Preliminary Use of Endoluminal Ultrasonography in Assessment of Middle Ear with Effusion, by Chih-Hsiu Wu, MD, Chuan-Jen Hsu, MD, DMSc, Fon-Jou Hsieh, MD, American Institute of Ultrasound in Medicine, Journal vol. 17, pp. 427-430, dated 1998.

*Primary Examiner*—Francis J. Jaworski
(74) *Attorney, Agent, or Firm*—Pearne & Gordon LLP (57) ABSTRACT

An apparatus and method for detecting an ear disorder. The apparatus includes structure for transmitting and receiving a plurality of signals to interact with an ear, and includes structure for directing the plurality of signals along different directions. In one example, the apparatus includes a plurality of transducers, each for interacting with a different ear portion. The transducers may be in a curved array. A determination as to which of the transducers is operable to provide an accurate indication of the detected ear disorder can be made. The transducers can be operated sequentially. In general, the method includes transmitting and receiving a plurality of signals to interact with an ear for ear disorder detection, and directing the plurality of signals along different directions. In one example the method includes providing a probe that has a plurality of transducers for use in detecting the ear disorder.

47 Claims, 3 Drawing Sheets

U.S. PATENT DOCUMENTS

| | | | |
|---|---|---|---|
| 6,126,614 A * | 10/2000 | Jenkins et al. | 600/549 |
| 6,398,736 B1 * | 6/2002 | Seward | 600/466 |
| 6,544,187 B1 | 4/2003 | Seward | |
| 6,631,287 B1 * | 10/2003 | Newman et al. | 600/474 |
| 2003/0171655 A1 * | 9/2003 | Newman et al. | 600/200 |
| 2004/0167404 A1 * | 8/2004 | Bessler | 600/443 |

* cited by examiner

ULTRASONIC DETECTION OF EAR DISORDERS

RELATED APPLICATIONS

Benefit of prior Provisional Patent Application Ser. No. 60/432,191, filed Dec. 6, 2002, and Provisional Patent Application Ser. No. 60/442,869, filed Jan. 27, 2003, is hereby claimed, and the disclosures of these Provisional patent applications are expressly incorporated herein by reference.

FIELD OF THE INVENTION

The present invention relates to detection of at least one ear disorder. More particularly, the present invention relates to an apparatus and method for accurate detection via the use of plural transducers.

BACKGROUND OF THE INVENTION

Ear disorders are common afflictions affecting many people. For example, otitis media (OM), an inflammatory process of the middle ear, is the most common clinical condition seen by pediatricians in children 15 years old and younger. OM is characterized by the presence of middle ear effusion (MEE), a middle ear infection. Complications of undiagnosed OM can include hearing loss and consequently delay in the development of speech and language skills. The combination of the gravity of the complications of undiagnosed OM and an unsatisfactory, noninvasive diagnostic technique often leads to unnecessary over medication of children with antibiotics.

The most reliable determination of the presence of MEE is direct surgical exploration (myringotomy). This is accomplished by making a small incision in the tympanic membrane followed by fluid aspiration. It is an invasive procedure and must be performed in a surgical setting under anesthesia. None of the existing non-invasive methods for determining the presence of MEE achieve 100% agreement with myringotomy. In order to reduce unnecessary antibiotic use and assuring at the same time effective and complication-free treatment of patients with OM, there is an urgent need to develop a simple but more accurate method for non-invasive method for MEE detection.

BRIEF SUMMARY OF THE INVENTION

In accordance with one aspect, the present invention provides an apparatus for detecting an ear disorder. The apparatus includes means for transmitting and receiving a plurality of signals to interact with an ear for ear disorder detection. The apparatus includes means for directing the plurality of signals along a plurality of different directions to interact with different ear portions. The apparatus includes means for determining which received signal provides an accurate indication of the detected ear disorder.

In accordance with another aspect, the present invention provides an apparatus for detecting an ear disorder. The apparatus includes a plurality of transducers. Each transducer is operable to transceive a signal for ear disorder detection. The apparatus includes means for supporting the transducers in an array to interact with an ear, with each transducer being oriented along a different direction for interaction with a different ear portion during operation. The apparatus includes means for determining which of the transducers is operable to provide an accurate indication of the detected ear disorder.

In accordance with another aspect, the present invention provides an apparatus for detecting an ear disorder. The apparatus includes a plurality of transducers. Each transducer is operable to transceive a signal for ear disorder detection. The apparatus includes means for supporting the transducers in an array to interact with an ear, with each transducer being oriented along a different direction for interaction with a different ear portion during operation. The apparatus includes means for controlling the transducers to operate sequentially.

In accordance with another aspect, the present invention provides an apparatus for detecting an ear disorder. The apparatus includes a plurality of transducers. Each transducer is operable to transceive a signal for ear disorder detection. The apparatus includes means for supporting the transducers in a curved array.

In accordance with another aspect, the present invention provides a method of detecting an ear disorder. The method includes transmitting and receiving a plurality of signals to interact with an ear for ear disorder detection. The method includes directing the plurality of signals along a plurality of different directions to interact with different ear portions. The method includes determining which received signal provides an accurate indication of the detected ear disorder.

In accordance with another aspect, the present invention provides a method of detecting an ear disorder. The method includes providing a probe that includes a plurality of transducers. The method includes interacting the probe with an ear. The method includes operating the plurality of transducers to provide information. The method includes determining the existence of an ear disorder using the information In accordance with yet another aspect, the present invention provides a method of detecting an ear disorder. The method includes providing a probe that includes a plurality of transducers arranged in a curved array. The probe is interacted with an ear. The existence of an ear disorder is determined.

DESCRIPTION OF EXAMPLE EMBODIMENTS

Figure 1:
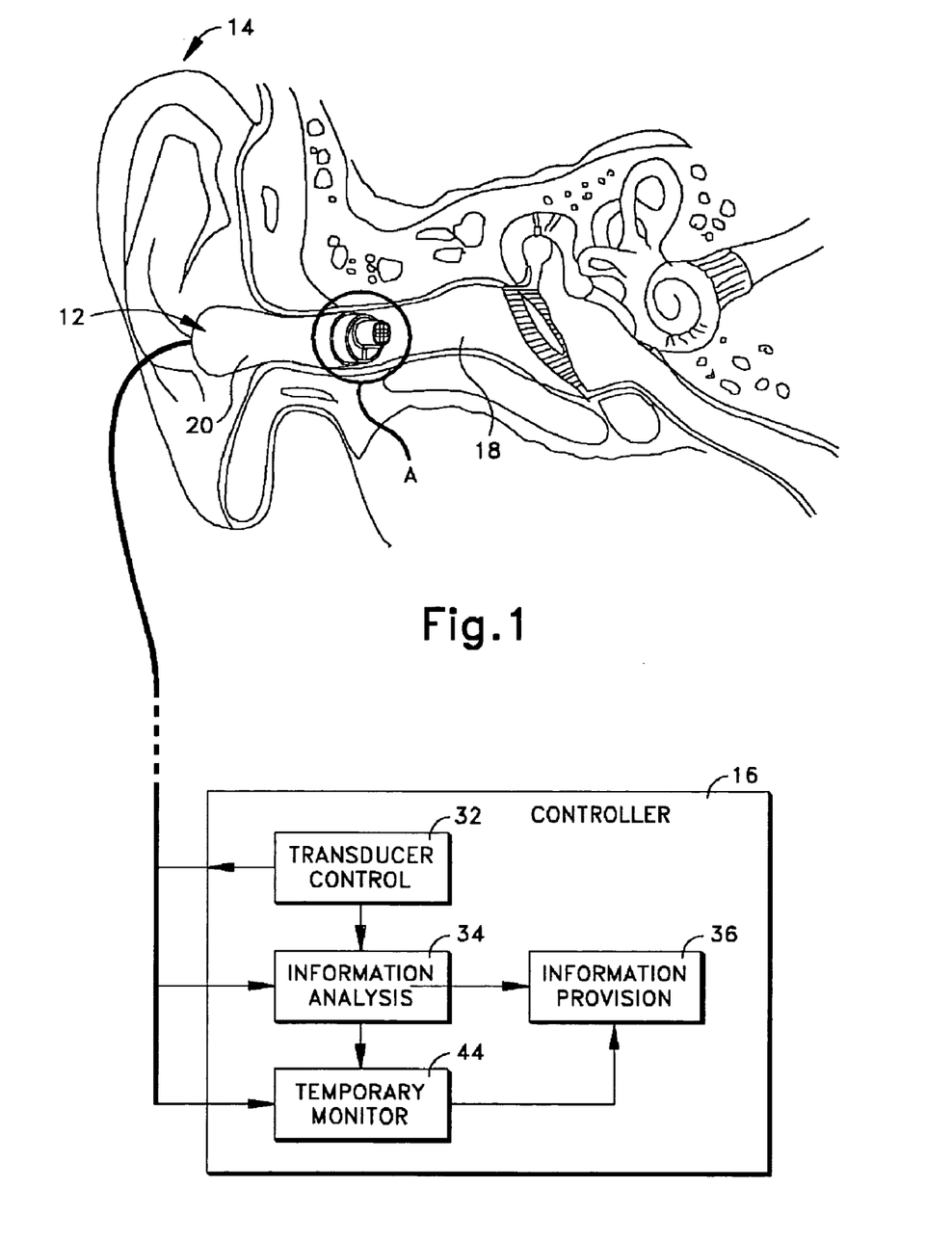
FIG. 1 is a schematic and pictorial view of an example apparatus interacting with an ear in accordance with the present invention.

An example of an apparatus 10 for the detection of ear disorders, such as middle ear effusion (MEE), etc., in accordance with the present invention, is shown in FIG. 1. The apparatus 10 includes a probe 12 that interacts with an ear 14. The apparatus 10 also includes structure 16 (e.g., components) for operation control, information analysis, information provision to a user (e.g., a medical examiner) of the apparatus, and possibly other functions.

The structure 16 associated with the control, analysis, provision, etc. is schematically shown in FIG. 1. Hereinafter, the schematically shown structure 16 is referred to as a controller 16, with an understanding that multiple functions can be performed by the controller. It is to be understood that the controller 16 can have a variety of designs, configurations, etc. Further, it is to be understood that specifics concerning the controller 16 are not intended to be limitations on the present invention. Any structure and/or configuration capable of performing the functions described herein may be utilized. Such variation of the structure is intended to be within the scope of the present invention.

Turning to the probe 12, the probe interacts with the ear 14 and may be inserted into (e.g., penetrate into the space of) a canal 18 of the ear. A conformable sleeve 20 may be provided to encapsulate all or a substantial portion of the probe 12. The sleeve 20 provides conformability and comfort, and helps enable the probe 12 to be useable with a variety of ear sizes. The sleeve 20 may be made of any material suitable to allow such conformability and comfort, such as silicone or polyurethane elastomers.

It is to be appreciated that the probe 12 may have a variety of shapes, configurations, etc. For example, the probe may be configured as an earmuff or headphone arrangement.

In one example, the probe 12 (FIG. 2) includes a plurality of sensors 26 supported thereon. In one preferred example, the sensors 26 are transducers 26. Also, in one specific example, the transducers 26 are ultrasonic transducers. Any number of transducers 26 may be utilized.

Each transducer is able to transceive an ultrasonic signal (e.g., a wave beam). Specifically, each transducer is able to transmit an ultrasonic signal and is able to receive the ultrasonic signal that is reflected back to the transducer. For each transducer, the output of an ultrasonic signal is in response to an electrical stimulus signal, and the receipt of the reflected signal results in a return electrical signal. The operation of each transducer to output the associated signal can be referred to as "firing."

In one example, each transducer has a center frequency in the range of 1–60 MHz (i.e., the output signal has such a frequency). The transducers 22 may be made from known materials and by known methods. However, newly developed materials and methods may be used.

Each reflected signal that is received conveys information (e.g., data) concerning the surface from which the signal was reflected. Upon interaction of the probe 12, having the included transducers 26, with the ear 14 (FIG. 1), the signals are reflected from surfaces within the ear. For example the signals may reflect from the tympanic membrane within the ear 14. As an example of the information conveyed via the reflected signal, amplitude of the reflected signal can be used to predict a fluid state within a middle ear portion of the ear 14. Such fluid state within the middle ear can be associated with an ear disorder. In the case of effusion, a second echo reflected from the middle ear cavity provides information concerning an ear disorder.

The transducers 26 (FIG. 2) on the probe 12 are arranged in an array 28. Within the present example, the array has an outer diameter of less than 5 mm. In accordance with one aspect of the present invention, each transducer within the array 28 is oriented along a different direction. Specifically, each transducer is oriented such that the associated signal is output along a direction that is different from directions associated with the other transducers. As a corollary, the receipt of the reflected signal back to each transducer is generally along the same direction. The output and receipt of a signal along a direction can be thought of as "aiming" the signal along a beam angle.

It is to be appreciated that all constructions and/or methodologies for directing the signals are intended to be within the scope of the present invention. For example, the probe 12 may have just a single transducer and a means, such a mechanical device or some other directing arrangement, to direct or target each subsequently transmitted signal toward a different ear portion. Such an arrangement could be considered to be a scanner. The targeting could sweep signals over an area of the ear.

Figure 3:
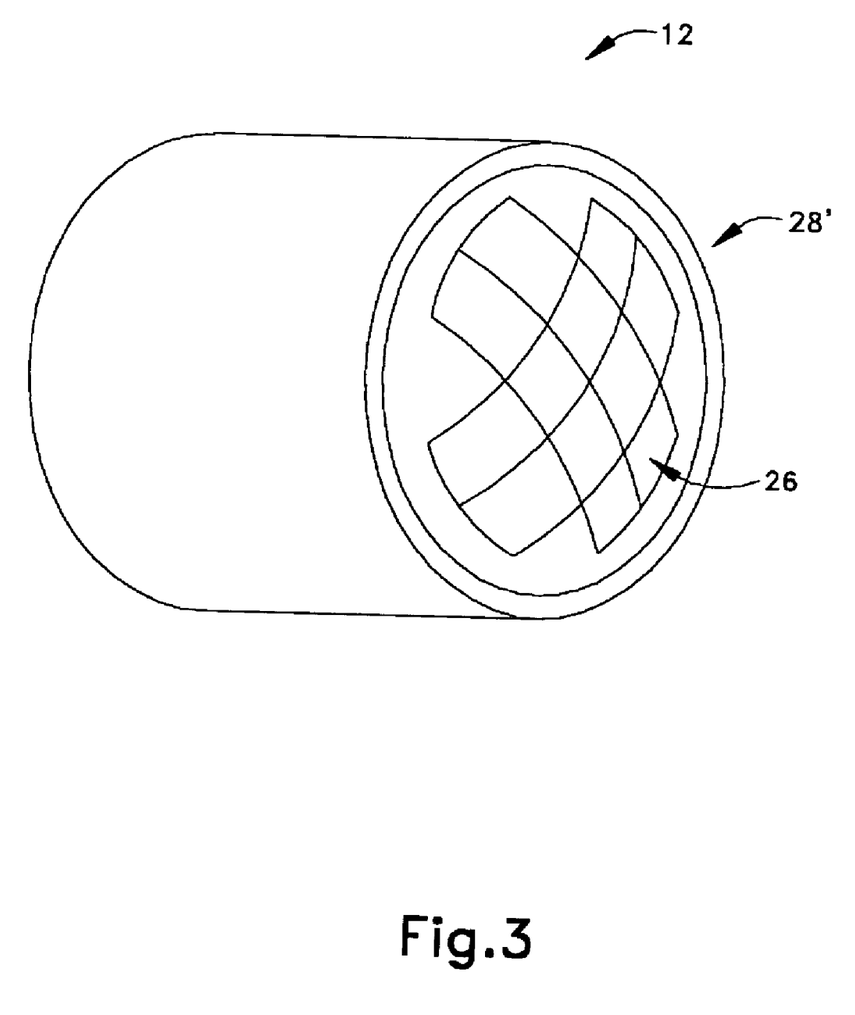
FIG. 3 is a partially schematic enlarged view of a curved array of transducers for the apparatus of FIG. 1.

In one example, which is shown in the FIG. 3, the orientation includes placement of the transducers 26 in a curved array 28' on the probe 12. Specifically, the transducers 22 are placed on a semispherical end surface portion of the probe 12. Alternatively, the transducers 22 may be arranged in some other non-planar fashion, with some means (e.g., varied orientation) to provide the differing direction. However, the curved array 28' arrangement provides a readily obtainable effect of each transducer being aimed at a different beam angle.

It has been noted by the inventor that because of the complex geometry of the ear, only ultrasonic signals (e.g., beams) originating from certain beam angles will produce useful data. Therefore, the orientation along different directions (e.g., curved array 28') of transducers 22 ensures that an ideal beam angle will be present and will generate useful data.

Also, it is contemplated that a useful signal may be transmitted from a first transducer and received by a second transducer. Thus, more than one transducer would be utilized to produce useful data.

Further, in accordance with an aspect of the present invention, the transducers 22 may be operated (e.g., "fired") sequentially, rather than simultaneously. By firing sequentially, it can be determined which transducer is positioned at a most useful beam angle. In order to obtain the most accurate determination concerning ear disorder detection, the only data used is from the transducer determined to be at the most useful angle.

Turning to the controller 16 (FIG. 1), the controller includes a portion 32 for controlling operation of the transducers 26. In one example, the firing of each transducer is accomplished via the transducer control portion 32 providing the electrical stimulus signal to the respective transducer. The controller 16 also receives the return electrical signals upon receipt of the return ultrasonic signals at the transducers 26. Within the one example, the control of operation by the transducer control portion 32 is such that the transducers 26 are sequentially fired.

Of course, the control provided by the transducer control portion 32 would be appropriate to the number, type, etc. of transducer(s), and would control other aspects such as a targeting arrangement as needed.

The controller 16 includes a portion 34 for analyzing the information conveyed within the reflected signal (e.g., one or more characteristics of the reflected signal) and transmitted to the controller via the electrical return signal. As one example, the information analysis portion 34 can analyze the reflected signal amplitude. As a specific example, the viscosity of fluid contained in the ear can be determined, such as by analysis of the reflected signal amplitude. However, it is to be understood that other determinations concerning ear disorders can be made. For example, non-fluid viscosity determinations are possible. Also, it is possible that ear disorders that are not related to fluid viscosity can be discerned. Further, aspects other than viscosity can be discerned concerning the fluid within the ear.

Of course, the analysis provided by the information analysis portion 34 would be appropriate to the number, type, etc. of transducer(s), and could factor in other aspects such as targeting, as needed. For example, the information analysis portion 34 may provide analysis of signals transmitted from a first transducer and received at a second transducer.

Also, the controller 16 includes a portion 36 for providing analysis information to the user of the apparatus 10. The information provision portion 36 may include a display 36 from which the user may discern the information.

The information analysis portion uses the signal information to determine if an ear disorder exists. In one example, only the signal from only one transducer is used to determine an accurate indication for the ear disorder detection. The utilized signal is based upon selection of a transducer that provides the best indication. The best indication is logically the transducer that is directed toward a certain portion of the ear for reflection therefrom. In one example, the certain portion is the tympanic membrane. As such, the information analysis portion 34 determines which transducer is directed at the certain ear portion (i.e., the tympanic membrane) via signal analysis.

The signal analysis can be made easy via control the transducers to operate sequentially. The use of a sequential operation approach allows analysis without conflict from other signals. The transducer control portion 32 and the information analysis portion 34 of the controller 16 can thus interact and cooperate to accomplish this feature. However, it is to be appreciated that certain aspects of the present invention may not be limited to single transducer signal use for disorder determination and/or sequential operation.

One specific example of the apparatus 10 may include a temperature sensing means 42 (FIG. 2) that is operatively connected to a temperature monitoring portion 44 (FIG. 1) of the controller 16. The temperature sensing means 42 may be attached to or integrated with the probe 12 so that temperature measurements of the ear 14 may be taken in connection with operation of the transducer array 28. The temperature sensing means 42 may be, for example, a thermometer or other suitable device known in the art. The monitoring portion 44 is operatively connected to the information provision portion 36 such that the temperature information is also provided to the user.

Figure 2:
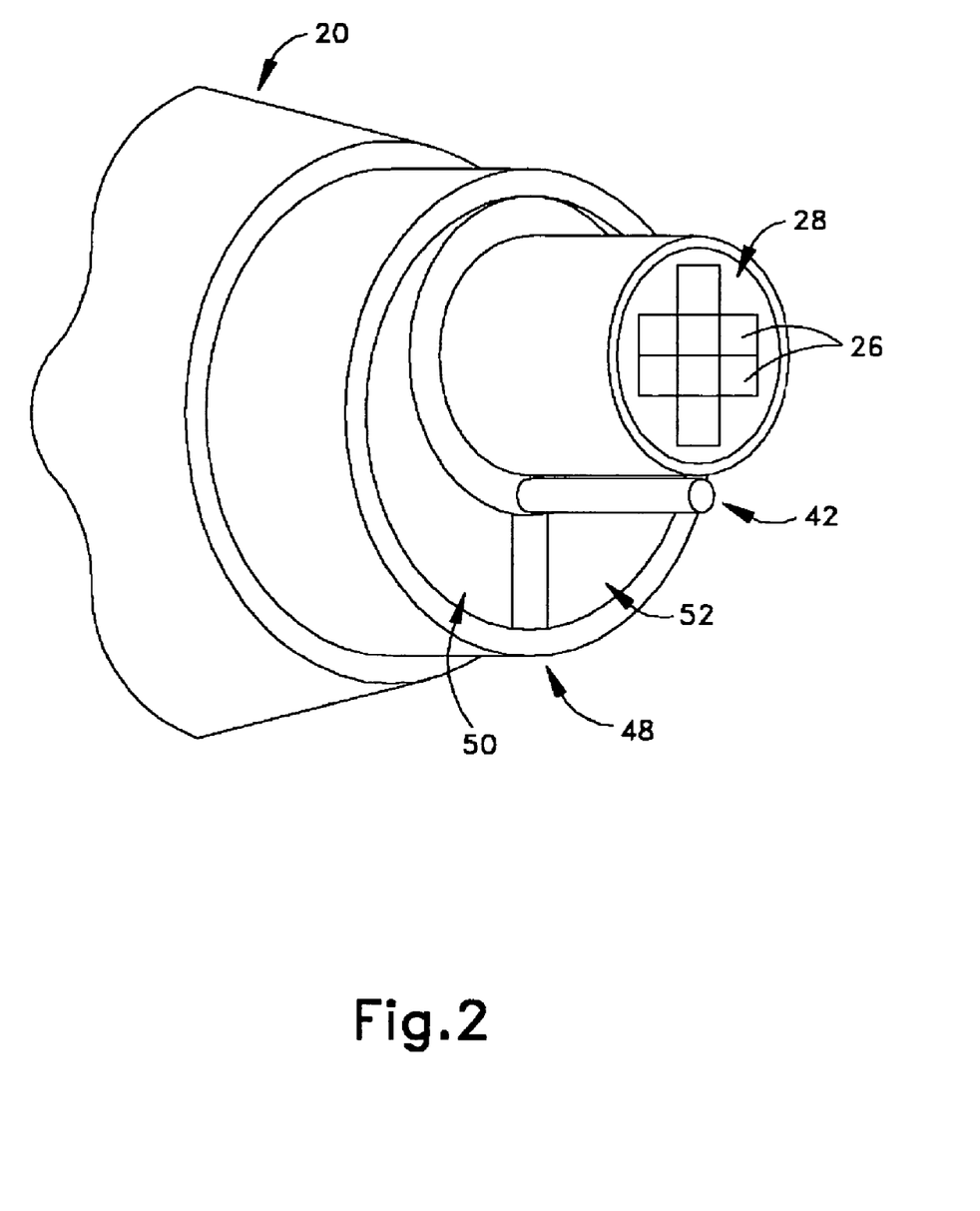
FIG. 2 is a partially schematic enlarged view of area A of FIG. 1 and shows details of one example of an array of transducers for the apparatus of FIG. 1 along with other components.

Another specific example of the apparatus 10 may include a fluid delivery system 48 (FIG. 2) for delivering and removing ultrasound transmitting medium to and from the canal 18 (FIG. 1) of the ear 14. The ultrasound transmitting medium may, inter alia, aid in acoustic coupling between the ear 14 and the transducers 26 and may comprise, for example, water, saline, commercially available known mediums, such as AYR-SALINE, NASAL-GEL or VO-SOL, etc. As shown in the Example of FIG. 2, the fluid delivery system 48 may be included within the probe 12. Such an example of the fluid delivery system 48 may include an ultrasound transmitting medium outlet 50 and an ultrasound transmitting medium inlet 52. The outlet 50 provides a conduit by which ultrasound transmitting medium may be delivered to the ear 14 and into the ear canal 18. The inlet 52 provides an evacuation component by which the ultrasound transmitting medium may be removed from the ear 14. The outlet 50 and inlet 52 may be connected, for example, by flexible tubing to external devices, such as a reservoir for containing the ultrasound transmitting medium. The use of flexible tubing may be advantageous in examinations involving pediatric patients because such flexible tubing permits the patient to retain movement of the head during data acquisition.

It is to be appreciated that the apparatus 10 may have any suitable configuration, set-up, etc. In FIG. 1, shown components of the controller, (e.g., the transducer control portion 32, the information analysis portion 34, and the information provision portion 36) are schematically depicted as being separate from the probe. However, it is to be understood that the apparatus 10 may be embodied in other suitable forms, such as a self-contained hand-held unit that directly incorporates such components as the transducer control portion 32, the information analysis portion 34, and the information provision portion 36. Also, the apparatus 10 may include additional components.

As another aspect of the present invention, one or more ear disorders are detected by a method. In one example, the method includes the steps of providing a probe that includes a plurality of transducers, interacting the probe with an ear, operating the plurality of transducers to provide information, and determining the existence of an ear disorder using the information. In another example, the method includes providing the probe 12, which includes the plurality of transducers 26 (e.g., arranged in a curved array 28'). The probe 12 is interacted with the ear 14, and the existence of an ear disorder is determined. The method may further include any of the following steps: sequentially firing the transducers 26, inserting into the ear canal 18, providing an ultrasound transmitting medium to the ear, evacuating the ultrasound transmitting medium from the ear canal, and/or measuring the temperature of the ear 14. Further, it is contemplated that this method can be performed within a relatively short time period (e.g., 60 seconds or less).

It is to be appreciated that the present invention provides ultrasonic detection of ear disorders. As such, the present invention provides a method and apparatus 10 for the investigation of the viscous state of fluid in an ear. The fluid in an ear may be described as serous (thin), purulent (medium), or mucoid (thick). Via one embodiment of the present invention, the apparatus 10 is able to distinguish whether the fluid in the ear is serous, purulent or mucoid. It has been found that pulse echo amplitudes can be used to predict the fluid state. For example, the first and second pulse amplitudes can be used to identify the mucoid state of the fluid. For a further example, a binary logic regression model fitted to the mucoid (yes/no) response as a function of the first and second pulse amplitude was able to correctly distinguish the yes/no mucoid states of all possible experimental yes/no pairings with a high accuracy, such as 100% accuracy.

An example of the methodology and observations therefrom regarding the investigation of the viscous state of fluid in an ear will now be discussed. Concentration of mucin was determined as a significant factor determining viscosity of effusion. Artificial effusion was prepared from porcine stomach mucin (Sigma) dissolved in phosphate buffered saline (PBS). A series of "artificial MEE" solutions with concentrations between 0 and 10% (w/v) of mucin were tested.

Viscosities of the solutions were measured using Cannon-Fenske type capillary viscometers. Type A viscometer was used for measurements at low viscosity solutions, type B for middle range and type C for high viscosity range. Measurements were done in a thermostatically controlled cell at 25° C. Viscosities of tested solutions were calculated using capillary constants values from manufacturer-provided calibration certificates. A series of "artificial MEE" solutions with concentrations between 0 to 10% (w/v) of mucin were prepared.

Correlation between viscosity of fluid and amplitude has logarithmic character, i.e., higher sensitivity to viscosity changes in the low viscosity range. This relation may be favorable for the present invention because there is likely a rather small viscosity difference between serous and purulent effusion, which are in the low viscosity range. Viscosity of mucoid fluid is likely significantly higher than either of serous of purulent so even if it falls into the lower sensitivity part of the curve it remains detectable. Tested viscosity range of kinematic viscosity was between 0.98 cSt (PBS) and 168 cSt (10% mucin solution in PBS).

As the ultrasonic signal propagates through the medium, the energy of the signal is absorbed and therefore the intensity decreases with the distance. The decrease of peak pressure with distance is described by the equation:

$$p(x)=p_o \exp(-\alpha x)$$

wherein x is distance, $\alpha$ is the attenuation coefficient of the medium, and $p_o$ is pressure at x=0.

The attenuation coefficient $\alpha$ depends on the frequency of the signal. In the case of Newtonian fluids, $\alpha$ is proportional to the second power of frequency.

Attenuation of the ultrasonic signal traveling through the medium can be expressed as the energy loss of the signal per unit distance. An ultrasonic signal traveling though different layers of tissue also loses energy due to the reflections from the interfaces between sections having different values of characteristic impedance. The energy loss of the traveling signal is due to reflection and can be distinguished from the energy loss due to attenuation since reflection coefficients are frequency independent.

The coefficient of attenuation, $\alpha$, however, depends on the signal frequency as described by equation:

$$\alpha(f)=\alpha_o f^n$$

where $\alpha$ is the frequency dependent attenuation coefficient of the medium, f is the signal frequency, and n and $\alpha_o$ are attenuation coefficients characteristic to the medium. For Newtonian fluids, n=2.

Viscosity of MEE changes at different stages of the disease from low (purulent effusion) to high (mucoid) with intermediary serous effusion. While low viscosity purulent fluid indicates AOM with high chance of clearing without surgical intervention, presence of high viscosity mucoid fluid may be the indication for tube placement.

The energy of the ultrasonic signal traveling through the middle ear is attenuated by the effusion according to the above equation. In consequence, the amplitude is related to the viscosity of the effusion and the width of the middle ear. The width can be calculated from the delay of the membrane echo and middle ear echo.

In summary, it is to be appreciated that the present invention can provide for MEE detection by analysis of ultrasonic signals generated from miniature transducers arranged in a curved array. The MEE detection may be non-invasive and may be performed on a conscious patient without the need for anesthesia. The ultrasonic detection of MEE is based on the analysis of the ultrasonic signal reflected (e.g., an echo) from the tympanic membrane and, in the case of effusion, a second echo reflected from the middle ear cavity. In the case of a normal ear, a significant portion of the ultrasonic signal energy is reflected due to the mismatch between acoustic impedance of the tympanic membrane and the impedance of air filling the middle ear cavity. When the effusion is present, the energy of a reflected pulse is significantly lower. This is due to the good match of impedances of the tympanic membrane and the fluid, which allows the pulse to penetrate into the middle ear cavity.

It should be evident that this disclosure is by way of example and that various changes may be made by adding, modifying or eliminating details without departing from the fair scope of teaching contained in this disclosure. In particular, the discussion, equations and methodology presented herein is by way of example only and other variations are contemplated and considered within the scope of the invention.

The invention claimed is:

1. An apparatus for detecting an ear disorder, the apparatus including:
   means for transmitting and receiving a plurality of signals to interact with an ear for ear disorder detection;
   means for directing the plurality of signals along a plurality of different directions to interact with different ear portions;
   means for determining which received signal provides an accurate indication of the detected ear disorder and for determining that other received signals can be discarded; and
   means for detecting the ear disorder using the signal determined as providing an accurate indication of the detected ear disorder.

2. An apparatus as set forth in claim 1, wherein the means for transmitting includes a plurality of transducers.

3. An apparatus as set forth in claim 1, wherein the means for transmitting includes at least one transducer.

4. An apparatus as set forth in claim 1, wherein the means for directing includes means for targeting the signals toward different ear portions.

5. An apparatus for detecting an ear disorder, the apparatus including:
   a plurality of transducers, each transducer being operable to transmit and receive a signal for ear disorder detection;
   means for detecting the ear disorder using only one of the received signals;
   means for supporting the transducers in an array to interact with an ear, with each transducer being oriented along a different direction for interacting with a different ear portion during operation; and
   means for determining which of the transducers is operable to provide an accurate indication of the detected ear disorder.

6. An apparatus as set forth in claim 5, wherein the means for supporting includes means for supporting in a curved array.

7. An apparatus as set forth in claim 5, wherein the means for determining includes means for determining which transducer is directed at a certain ear portion.

8. An apparatus as set forth in claim 5, including means for controlling the transducers to operate sequentially.

9. An apparatus as set forth in claim 8, wherein the means for controlling and the means for determining operate cooperatively such that each transducer is operated to transceive the associated signal without conflict from other signals.

10. An apparatus as set forth in claim 5, wherein the transducers are ultrasound transducers and the associated signal is an ultrasonic signal that is reflected from the respective ear portion, and the means for determining includes means for determining if the associated signal has reflected from a portion of an ear drum of the ear.

11. An apparatus as set forth in claim 10, including means for determining characteristics of a second echo from a middle ear of the ear.

12. An apparatus as set forth in claim 5, including means for using only the signal from only one transducer determined to provide an accurate indication for the ear disorder detection.

13. An apparatus as set forth in claim 5, wherein the transducer determined to be operable to provide an accurate indication of the detected ear disorder receives a signal transmitted from another transducer to provide the accurate indication.

14. An apparatus for detecting an ear disorder without imaging the ear and without temperature sensing of the ear, the apparatus including:
a plurality of transducers, each transducer being operable to transceive a signal for ear disorder detection without imaging of the ear and without temperature sensing of the ear;
means for supporting the transducers in an array to interact with an ear, with each transducer being fixedly oriented along a different direction for interacting with a different ear portion during operation; and
means for controlling the transducers to operate sequentially.

15. An apparatus as set forth in claim 14, wherein the means for supporting includes means for supporting in a curved array.

16. An apparatus as set forth in claim 14, including means for determining which of the transducers is operable to provide an accurate indication of the detected ear disorder.

17. An apparatus as set forth in claim 16, wherein the means for determining which of the transducers is operable to provide an accurate indication of the detected ear disorder includes means for determining which transducer has received a signal transmitted from another transducer that is usable to provide an accurate indication of the detected ear disorder.

18. An apparatus as set forth in claim 16, wherein the means for determining includes means for determining which transducer is directed at a certain ear portion.

19. An apparatus as set forth in claim 16, wherein the means for controlling and the means for determining operate cooperatively such that each transducer is operated to transceive the associated signal without conflict from other signals.

20. An apparatus as set forth in claim 16, wherein the transducers are ultrasound transducers and the associated signal is an ultrasonic signal that is reflected from the respective ear portion, and the means for determining includes means for determining if the associated signal has reflected from a portion of an ear dwm of the ear.

21. An apparatus as set forth in claim 20, including means for determining characteristics of a second echo from a middle ear of the ear.

22. An apparatus as set forth in claim 16, including means for using only the signal from only one transducer determined to provide an accurate indication for the ear disorder detection.

23. An apparatus for detecting an ear disorder, the apparatus including:
a plurality of transducers, each transducer being operable to transceive a signal for ear disorder detection;
means for supporting the transducers in a curved array; and
means for detecting the ear disorder using only one received signal, and Means for determining which of the transducers is operable to provide an accurate indication of the detected ear disorder.

24. An apparatus as set forth in claim 23, including means for controlling the transducers to operate sequentially.

25. An apparatus as set forth in claim 23, wherein the means for determining which of the transducers is operable to provide an accurate indication of the detected ear disorder includes means for determining which transducer has received a signal transmitted from another transducer that is usable to provide an accurate indication of the detected ear disorder.

26. An apparatus as set forth in claim 23, wherein the means for determining includes means for determining which transducer is directed at a certain ear portion.

27. An apparatus as set forth in claim 23, wherein the transducers are ultrasound transducers and the associated signal is an ultrasonic signal that is reflected from the respective ear portion, and the means for determining includes means for determining if the associated signal has reflected from a portion of an ear drum of the ear.

28. An apparatus as set forth in claim 27, including means for determining characteristics of a second echo from a middle ear of the ear.

29. An apparatus as set forth in claim 23, including means for using only the signal from only one transducer determined to provide an accurate indication for the ear disorder detection.

30. A method of detecting an ear disorder, the method including:
transmitting and receiving a plurality of signals to interact with an ear for ear disorder detection;
directing the plurality of signals along a plurality of different directions to interact with different ear portions;
determining which received signal provides an accurate indication of the detected ear disorder and determining that other received signals can be discarded; and
detecting the ear disorder using the signal determined as providing an accurate indication of the detected ear disorder.

31. A method as set forth in claim 30, wherein the step of transmitting includes transmitting from a plurality of transducers.

32. A method as set forth in claim 30, wherein the step of transmitting includes transmitting from at least one transducer.

33. A method as set forth in claim 30, wherein the step of directing includes targeting the signals toward different ear portions.

34. A method of detecting an ear disorder that includes middle ear effusion, the method including:
providing a probe that includes a plurality of transducers;
interacting the probe with an ear;
operating the plurality of transducers to provide information; and
determining the existence of an ear disorder using the information to determine middle ear effusion without ear imaging.

35. A method as set forth in claim 34, wherein the step of determining includes using information derived from less than all of the transducers.

36. A method as set forth in claim 35, wherein the step of determining includes using information derived from only one transducer.

37. A method as set forth in claim 34, wherein the step of providing a probe includes orienting each transducer along a different direction for interaction with a different ear portion during operation.

38. A method as set forth in claim 34, wherein the step of providing a probe includes supporting the transducers in a curved array.

39. A method as set forth in claim 34, wherein the step of determining includes determining which of the transducers is operable to provide an accurate indication of the detected ear disorder.

40. A method as set forth in claim 39, wherein the step of determining which of the transducers is operable to provide an accurate indication of the detected ear disorder includes determining which transducer has received a signal transmitted from another transducer that is usable to provide an accurate indication of the detected ear disorder.

41. A method as set forth in claim 34, wherein the step of determining includes determining which transducer is directed at a certain ear portion.

42. A method of detecting an ear disorder, the method including:
    providing a probe that includes a plurality of transducers arranged in an array, which is curved in a first plane and which is curved in a second plane transverse to the first plane;
    interacting the probe with an ear; and
    determining the existence of an ear disorder.

43. A method as set forth in claim 42, wherein the step of determining includes using information derived from less that all of the transducers.

44. A method as set forth in claim 43, wherein the step of determining includes using information derived from only one transducer.

45. A method as set forth in claim 42, wherein the step of determining includes determining which of the transducers is operable to provide an accurate indication of the detected ear disorder.

46. A method as set forth in claim 45, wherein the step of determining which of the transducers is operable to provide an accurate indication of the detected ear disorder includes determining which transducer has received a signal transmitted from another transducer that is usable to provide an accurate indication of the detected ear disorder.

47. A method as set forth in claim 42, wherein the step of determining includes determining which transducer is directed at a certain ear portion.

* * * * *

UNITED STATES PATENT AND TRADEMARK OFFICE
CERTIFICATE OF CORRECTION

PATENT NO. : 7,131,946 B2 Page 1 of 1
APPLICATION NO. : 10/729741
DATED : November 7, 2006
INVENTOR(S) : Lewandowski It is certified that error appears in the above-identified patent and that said Letters Patent is hereby corrected as shown below:

In Claim 20, Column 9, Line 45, please delete "dwm", and insert therefor --drum--.

Signed and Sealed this

Twenty-seventh Day of March, 2007

JON W. DUDAS
*Director of the United States Patent and Trademark Office*